United States Patent [19]

Richter

[11] Patent Number: 5,794,905

[45] Date of Patent: Aug. 18, 1998

[54] DEVICE FOR SUPPORTING ROD-LIKE OBJECTS

[76] Inventor: Herbert Richter, Drosselweg 8. 75331 Engelsbrand, Germany

[21] Appl. No.: 815,724

[22] Filed: Mar. 12, 1997

[51] Int. Cl.⁶ .................................................. A47G 1/10
[52] U.S. Cl. .................................. 248/316.4; 248/316.1
[58] Field of Search ........................ 248/316.4, 205.3, 248/231.41, 316.1, 228.3, 230.3

[56] References Cited

U.S. PATENT DOCUMENTS

| 2,535,563 | 12/1950 | Boyer et al. | 65/54 |
| 2,631,346 | 3/1953 | Wengen et al. | 24/81 |
| 3,509,882 | 5/1970 | Blake | 128/325 |
| 4,098,479 | 7/1978 | Hartstone et al. | 248/214 |
| 5,149,032 | 9/1992 | Jones et al. | 248/154 |
| 5,222,381 | 6/1993 | Wilcox | 70/19 |
| 5,323,992 | 6/1994 | Sifers et al. | 248/205.3 |
| 5,332,184 | 7/1994 | Davis | 248/231.4 |
| 5,582,377 | 12/1996 | Quesada | 248/229.12 |

*Primary Examiner*—Leslie A. Braun
*Assistant Examiner*—Kimberly T. Wood
*Attorney, Agent, or Firm*—Klaus J. Bach

[57] ABSTRACT

In a holder for supporting rod-like articles such as pens with a base body and a stationary clamping jaw mounted on the base body, a movable clamping jaw is slideably supported on the base body so as to be movable from and to the stationary clamping jaw and the base body has an elongated recess extending in the direction of movement of the movable clamping jaw and the movable clamping jaw has a cover plate which extends along the base body and into the stationary clamping jaw and has, its distal end, a nose-like projection projecting downwardly into the elongated recess where it is engaged by a compression spring disposed in the elongated recess and biased in a clamping jaw closing direction.

4 Claims, 2 Drawing Sheets

1

DEVICE FOR SUPPORTING ROD-LIKE OBJECTS

BACKGROUND OF THE INVENTION

The invention relates to a holder for supporting rod like objects, particularly pens or pencils, with a clamping structure for resiliently engaging the objects.

Such devices are generally used for supporting ball point pens or pencils. The clamping device comprises usually a U-shaped structure with narrow resilient legs which are arranged slightly spaced from one another and can be bent apart for receiving and engaging a pen therebetween.

Such structures, however, can accept pens of only certain diameter in order to properly engage the pens. If the pen diameter is too small, the retaining force is insufficient and if the pen diameter is tool large, the legs are bent apart whereby their relative angular position is changed so far that a pen can no longer be engaged.

As a result, use of such a holder is limited to pens of certain diameters. Different pens, that is pens of different diameters require different holders designed especially for the particular pens with which they are intended to be used. This of course is relatively expensive as it requires different tools for the manufacture and also the storage of different holders.

It is therefore the object of the present invention to provide a holder for rod-like objects wherein the objects are firmly engaged essentially with the same engagement force independently of their diameter.

SUMMARY OF THE INVENTION

In a holder for supporting rod-like articles such as pens with a base body and a stationary clamping jaw mounted on the base body, a movable clamping jaw is slideably supported on the base body so as to be movable to and from the stationary clamping jaw and the base body has an elongated recess extending in the direction of movement of the movable clamping jaw and the movable clamping jaw has a cover plate which extends along the base body and into the stationary clamping jaw and has at its distal end a nose-like projection projecting downwardly into the elongated recess where it is engaged by a compression spring disposed in the elongated recess and biased in a clamping jaw closing direction.

With the holder according to the invention, the distance between the two relatively movable jaws can be changed over a relatively large range while their relative orientation remains the same. A small diameter object is held over a larger circumference than a larger diameter object, but the compression force is smaller for the smaller diameter object than it is for the larger diameter object since, with the larger diameter object, the spring is compressed to a greater degree. The smaller and the larger diameter objects are therefore equally well retained and can be removed with essentially the same force.

The rod-like object holder according to the invention will be described below on the basis of the accompanying drawings.

DESCRIPTION OF A PREFERRED EMBODIMENT

Figure 1:
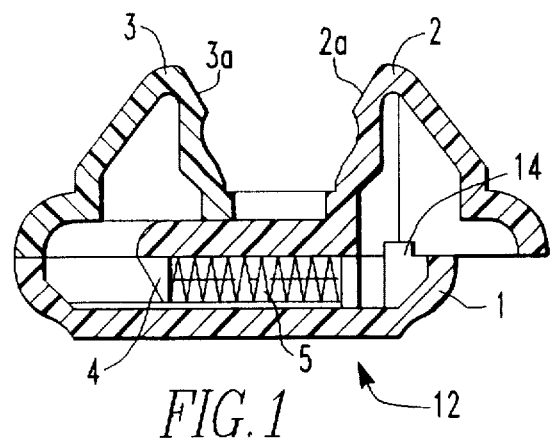
FIG. 1 is a cross-sectional view of the holder according to the invention wherein the clamping jaws are shown in a pulled-apart position.
Figure 2:
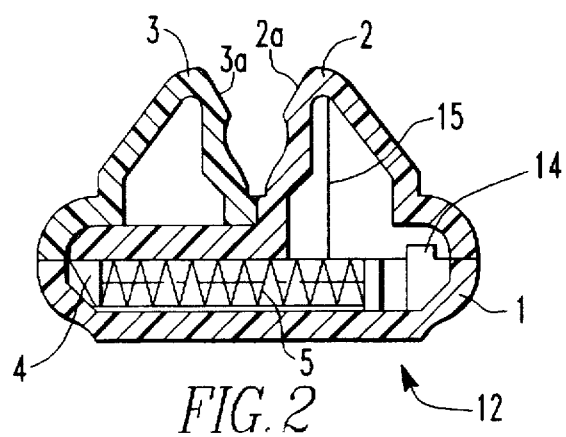
FIG. 2 shows the holder of FIG. 1 with the jaws in their closest position.
Figure 3:
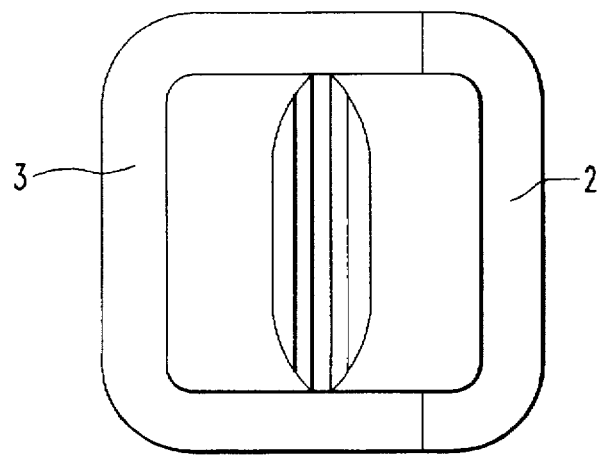
FIG. 3 is a top view of the arrangement as shown in FIG. 2.

As apparent from the figures, the pen holder according to the invention comprises a base body 1 on which two clamping jaws 2 and 3 are disposed. One of the clamping jaws that is clamping jaw 2 is slideably supported on the base body 1 whereas the other clamping jaw is firmly connected to the base body 1. For the connection with the base body 1, the clamping jaw 3 has pin-like projections 13a (FIG. 4) which are received in corresponding openings 13b (see FIG. 5) in the base body 1. The clamping jaw 2 includes a cover plate 9 together with which it is slideably supported on the base body 1.

The base body 1 has an enlarged recess 6 in which a compression spring 5 is disposed. At its front end, the recess 6 is delineated by an end wall 7 which includes a gap 8 of sufficient width to accommodate the nose-like projection 4.

The facing walls of the jaws 2 and 3 have end portions 2a, 3a which are disposed at an angle so as to form a wedge shaped entry area between the jaws. Further inward, they are provided with opposite longitudinally extending parallel recesses 10, 11 which, in cross-section, have the shape of a segment of a circle.

The base body 1 further has guide stubs 14 which extend into the clamping jaw 2 and which guide the slideable clamping jaw 2 and act as stops to limit its outward movement when the wall 15 formed inside the slideable clamping jaw 2 reached the stub 14.

At the bottom side, the base body 1 is provided with a self-adhesive surface 12.

Figure 4:
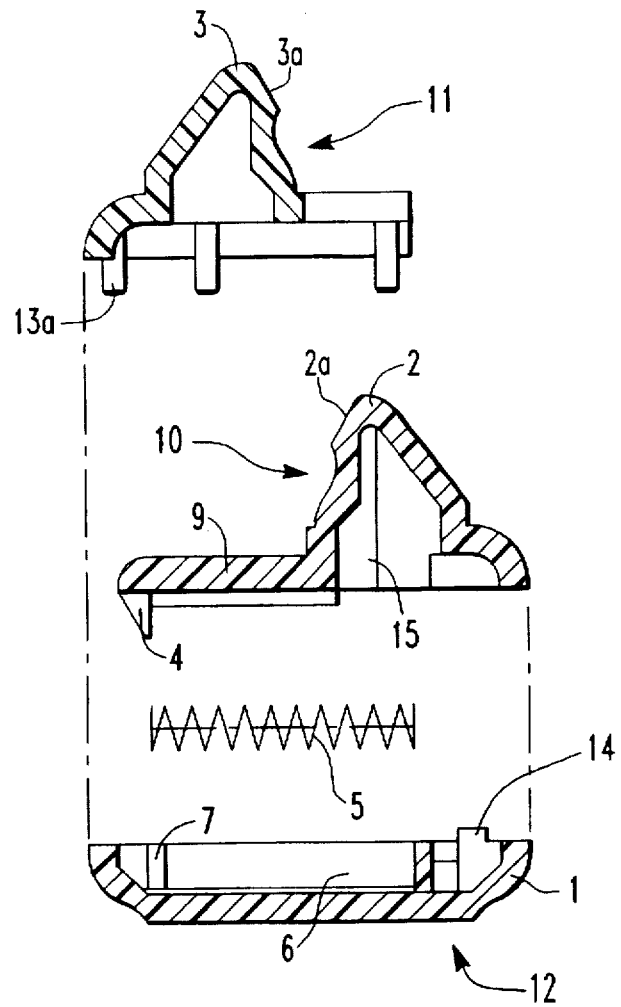
FIG. 4 is an exploded view of the holder shown in FIGS. 1–3 to clearly show the various parts.
Figure 5:
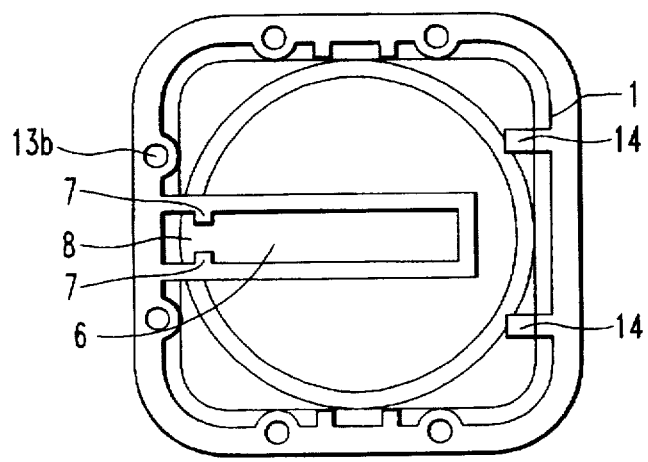
FIG. 5 is a top view of the base body of the holder with the jaws removed.

As apparent, particularly from FIGS. 4 and 5, the pen holder components are assembled by first placing the spring 5 into the elongated recess 6 of the base body 1. Then the clamping jaw 2 is placed onto the base body 1 such that its nose-like projection is disposed in the gap 8 outside the elongated recess 6 of the front end wall 7 against which the spring 5 bears. The slideable jaw 2 is then moved toward the guide stub 14 whereby the nose-like projection passes through the gap 8 of the front end wall 7 of the elongated recess and compresses the compression spring 5. Then the other clamping jaw 3 is mounted onto the base body such that the pin-like projections 13a are inserted into the opening 13b, wherein they are firmly engaged. The clamping jaws 2, 3 are so shaped that the cover plate 9 of the slideable clamping jaw 2 can move into the stationary clamping jaw 3.

The clamping jaw 2 is slideable on the base body 1 away from the stationary clamping jaw 3 against the force of the spring 5, for example, by pushing a pencil into the wedge-shaped space between the inclined end wall portions 2a and 3a of the jaws 2 and 3. When the pen or rod-like article is pushed inwardly into the area of the recesses 10 and 11, the spring moves the slideable clamping jaw 2 into engagement with the pen or rod-like article for holding the pen or rod-like body. However, the spring force can be easily overcome when the pen or rod-like body is removed.

With its self-adhesive surface, the holder according to the invention can be attached to any reasonably smooth surface such as the dash board of a car, a refrigerator and a computer housing. It has a pleasant shape and it has only softly rounded edges so that it is not prone to cause injuries. As mentioned earlier it may be use for holding pens and pencils. But it may also be used for holding other rod-like objects at locations were they are readily available such as tire gauges, pen-type flashlights or tools such as screw drivers.

What is claimed is:

1. A holder for supporting rod-like articles, comprising: a base body, a stationary clamping jaw firmly mounted on said base body, a movable clamping jaw slideably supported on said base body so as to be movable from and toward said stationary clamping jaw, said base body having an elongated recess formed therein so as to extend in the direction of movement of said movable clamping jaw, and said movable clamping jaw having a cover plate extending therefrom along said base body into said stationary clamping jaw and having at its distal end a nose-like projection extending downwardly into said elongated recess, and a compression spring disposed in said elongated recess, said elongated recess having front and rear end walls at opposite longitudinal ends thereof between which said compression spring is disposed and said front end wall adjacent said nose-like projection being provided with a gap sufficiently wide to permit passage of said nose-like projection such that said compression spring is engaged and compressed by said nose-like projection when said movable clamping jaw is moved away from said stationary clamping jaw.

2. A holder according to claim 1, wherein said clamping jaws have opposite clamping walls with inclined end portions so as to form a wedge-shaped entrance area and adjacent recesses which, in cross-section have the shape of a segment of a circle for receiving a rod-like article.

3. A holder according to claim 1, wherein said base body is provided with a stop for limiting outward movement of said movable clamping jaw.

4. A holder according to claim 1, wherein said base body has a bottom with a self-adhesive surface structure.

* * * * *